United States Patent [19]

Nunn et al.

[11] Patent Number: 5,794,848
[45] Date of Patent: Aug. 18, 1998

[54] HYGROSTAT AND SYSTEM

[75] Inventors: Kenneth Lawrence Nunn, Hampton Park; Robert Michael Wilson, Beaumaris, both of Australia

[73] Assignee: Moss Products Pty Ltd, South Clayton, Australia

[21] Appl. No.: 669,386
[22] PCT Filed: Jan. 2, 1996
[86] PCT No.: PCT/AU96/00002
    § 371 Date: Jul. 16, 1996
    § 102(e) Date: Jul. 16, 1996
[87] PCT Pub. No.: WO96/21143
    PCT Pub. Date: Jul. 11, 1996

[30] Foreign Application Priority Data

Dec. 30, 1994 [AU] Australia .................. PN0342

[51] Int. Cl.⁶ .................................... B05B 1/08
[52] U.S. Cl. .................................... 239/63
[58] Field of Search .............. 47/48.5; 137/78.3; 239/63, 542, 67

[56] References Cited

U.S. PATENT DOCUMENTS

| 3,204,872 | 9/1965 | Whear | 239/63 |
|---|---|---|---|
| 3,512,712 | 5/1970 | Benesch | 239/63 |
| 3,840,182 | 10/1974 | Geffroy | 239/145 |
| 3,874,590 | 4/1975 | Gibson | 239/63 |
| 4,095,458 | 6/1978 | Wild | 239/63 X |
| 4,182,357 | 1/1980 | Ornstein | 239/63 |
| 4,214,701 | 7/1980 | Beckmann | 239/63 |
| 4,648,555 | 3/1987 | Gumbmann | 239/63 |
| 4,696,319 | 9/1987 | Gant | 137/78.3 |
| 4,843,758 | 7/1989 | Raczkowski | 47/48.5 |
| 5,329,081 | 7/1994 | Jones | 200/61.04 |
| 5,368,235 | 11/1994 | Dozdoff et al. | 239/542 |

FOREIGN PATENT DOCUMENTS

| 532482 | 8/1978 | Australia . |
|---|---|---|
| 44772/79 | 10/1979 | Australia . |
| 33245/84 | 5/1985 | Australia . |
| 32237/84 | 2/1986 | Australia . |
| 31864/93 | 7/1993 | Australia . |
| 2224688 | 10/1974 | France . |
| 568513 | 10/1975 | Switzerland . |
| 2 017 868 | 10/1979 | United Kingdom . |
| 89/11787 | 12/1989 | WIPO . |
| 91/02455 | 3/1991 | WIPO . |

*Primary Examiner*—Kevin Weldon
*Attorney, Agent, or Firm*—Foley & Lardner

[57] ABSTRACT

A hygrostat system employs a hygroscopic element of a coherent polymer suitable for burying in soil near a plant (for example, a pot-plant). The hygroscopic element directly contacts the soil and has no lost motion as it expands and contracts so that the soil does not interpose itself at the ends of the element. In one embodiment, the hygrostate system has an upper chamber shaped like an inverted cup closed by a diaphragm and a lower frame shaped like an inverted stirrup having a lower arch and having an integrally-molded upper snapping ring, which fits inside the rim of the upper chamber. The upper chamber has a water inlet/outlet spigots extending therefrom. The hygroscopic element is strip shaped and is clipped or keyed at its lower end to a key-stone protrusion formed at the bottom of the lower frame. A pair of guide rails, which serve to stiffen the hygrostat element against buckling, extend from each side thereof. The upper ends of the rails are joined together by a foot to which the upper end of the hygroscopic element is attached and attached to the diaphragm by pull-though studs. The lower ends of the rails are free to slide over the keystone, and positioned laterally adjacent thereto.

10 Claims, 5 Drawing Sheets

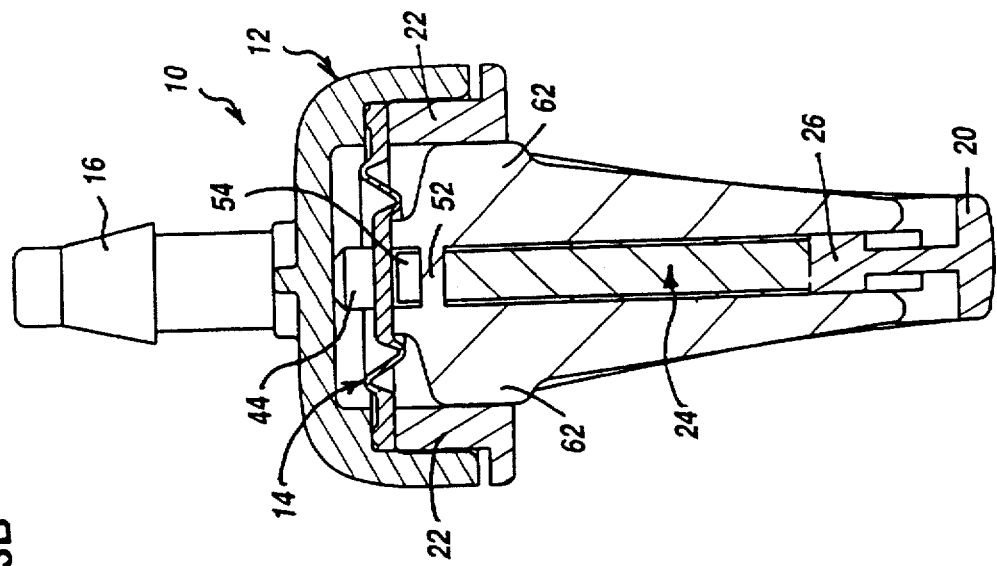
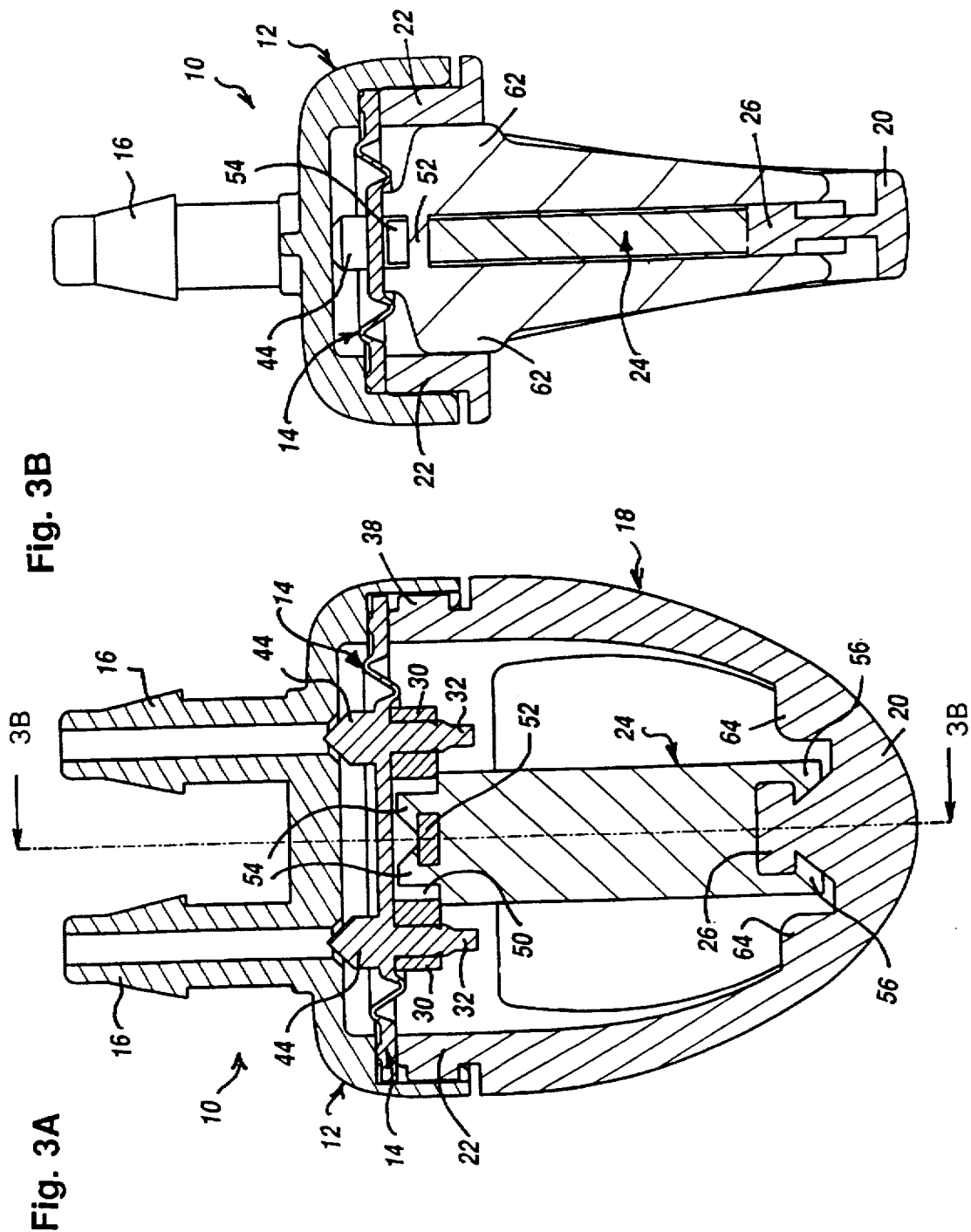

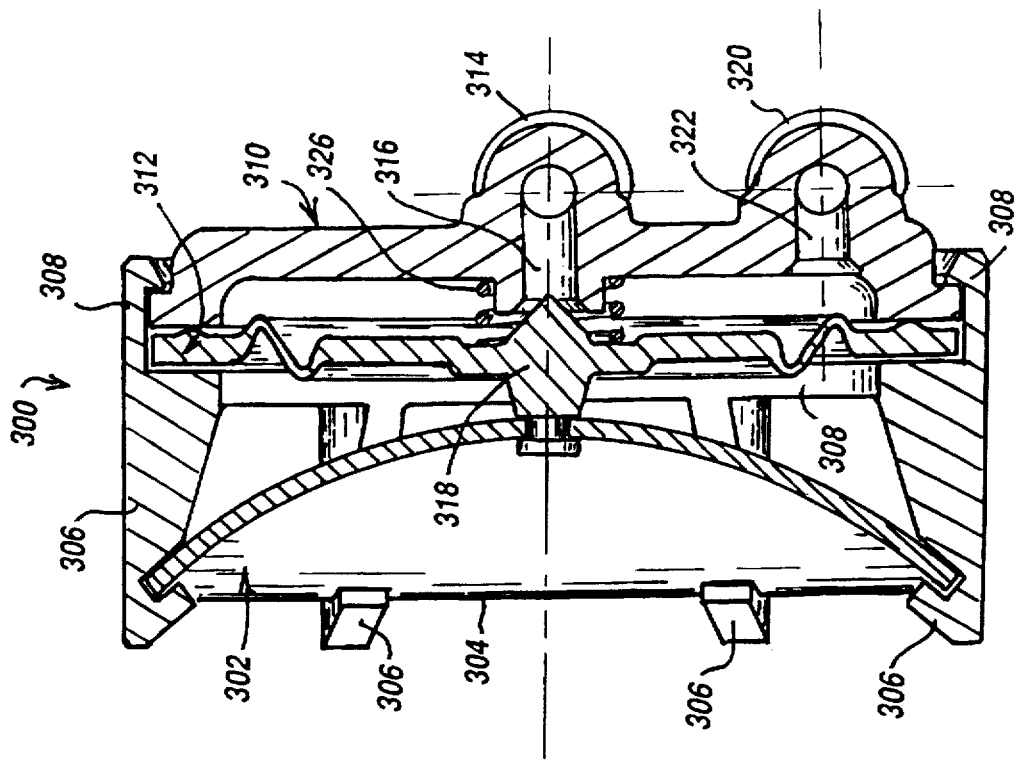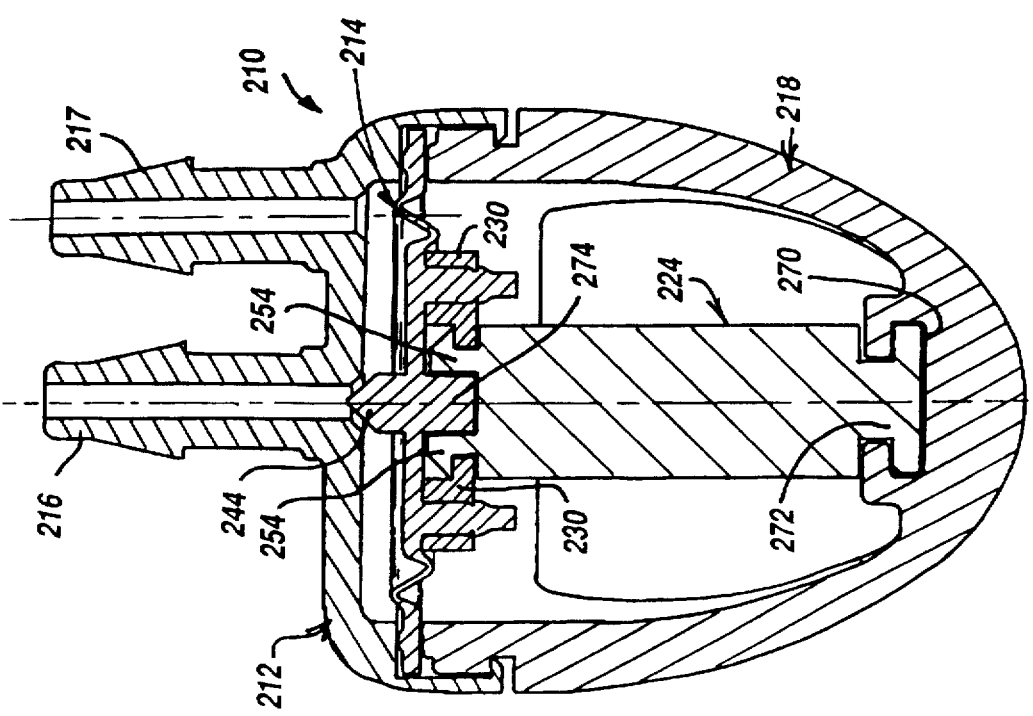

1

HYGROSTAT AND SYSTEM

TECHNICAL FIELD

This invention relates to hygrostats of the type where the lengthwise expansion and contraction of an elongate hydroscopic element (with the uptake and release of moisture) is employed to operate a valve or position transducer (including electrical switches) that may be used to control the flow of water, to operate an alarm or indicate the level of moisture in the hydroscopic element. The invention is also concerned with hygrostat systems and methods.

The invention is particularly, but not exclusively, concerned with the automatic supply of water to pot-plants and to individual plants in open soil where the hygrostat is buried in the soil near the plant. However, some hygrostat units of this invention may also be mounted above ground and used to inhibit timer-based sprinkler systems during and shortly after rain.

BACKGROUND TO THE INVENTION

In attempting to develop a hygrostat unit and system suited to indoor and outdoor pot-plants, we have found many problems that have not been adequately addressed by the prior art. For such a unit needs to be small and cheap and must operate with great reliability for long periods of time. It must be capable regulating very low water flow-rates under a variety of abnormal conditions, including independent over-watering, soil dry-out (when the water supply is cut off) and negative water pressure or 'suck-back' (which occurs when the water supply is lost and the system drains from the lowest opening).

We have found that most hydroscopic materials proposed in the art are quite unsuited to our purpose. Natural fibrous materials such as wood, paper, cork, leather or gut are highly variable, degenerate quickly in the soil and do not cycle in a repeatable manner. Most synthetic materials proposed in the art (e.g., polyacrylamide gels) also do not have good cyclic repeatability, they are so hydroscopic that they remain wet even when the soil is too dry for healthy plant growth, and they encourage root entanglement and fungal growth, which interfere with the operation of the hygrostat. We have also found that most prior art systems encase the hydroscopic element in such a manner as to create a micro-climate, which traps moisture. This problem may be further exacerbated by the release of water into the soil in the immediate vicinity of the hydrostat so that a column of mud forms around it. These factors result in poor and ineffectual regulation of the moisture content of the soil and, combined with the bulky nature of the devices, make such hygrostats wholly unsuited for use with pot-plants.

U.S. Pat. No. 3,204,872 to Whear discloses a hygrostat having a column of cork or wood mounted in a perforated metal container so that one end presses a diaphragm against an orifice to regulate the flow of water from an irrigation pipe into the ground immediately beneath the device, the container and pipe being buried in the soil. This device exhibits some of the problems mentioned above. That is, the wood or cork is bulky, has poor repeatability and quickly degrades in the soil. Also, the container creates a wet micro-climate not typical of the surrounding soil, the position at which the water is released tends to result in the 'column of mud' problem. Suck-back draws this mud into the hygrostat and dry-out (caused by loss of water-supply) results in mud and sand setting between the wood and the diaphragm and/or between the wood and the container so as to prevent proper operation of the device when water supply

2 is restored. The suck-back problem was addressed by U.S. Pat. No. 3,840,182 to Geffroy, which disclose the use of fine filters at the outlets. But these filters are subject to blockage.

Australian patent 523,482 to Beckmann discloses a hygrostat for use in regulating the flow of water through an above-ground hose, which passes through a transverse aperture in the top of a ground-spike that contains the hydroscopic element of wood or polyacrylamide gel. As the element absorbs moisture from the ground or from sprinklers, it expands to constrict the hose. However, these hygroscopic materials have poor repeatability. In one hygrostat disclosed by Beckmann, polyacrylamide gel is housed within an open-topped ceramic container, which draws in water by capillary action, causing the gel to expand and close a valve. If such a device were buried the ceramic container and its contents would act like a tensiometer and ensure that the gel remained wet after the surrounding soil became too dry. In fact, Beckmann suggests that a good part of the element should remain above ground. Evaporation to the atmosphere then plays a major role, and this will result in the accumulation of salts in and on the element.

Australian patent application 44772/79 by Ornstein employs a highly hydroscopic hydrogel to flatten a water-tube or operate a valve, water being drawn into the gel through a semi-permeable membrane that is strongly reinforced to prevent extrusion of the gel. U.S. Pat. No. 5,239,081 to Jones uses polyacrylamide gel beads in a semipermeable pouch within a cylinder to drive a spring-loaded piston and work an electrical switch. International patent application PCT/GB89/00643 by the University of Strathclyde employs a layer of gel between a semi-permeable membrane and an impermeable diaphragm to deflect the diaphragm and close a valve port. U.S. Pat. No. 4,696,319 to Gant uses bentonite clay in a cylinder behind a semi-permeable membrane to drive a piston against a spring to close a valve, while Australian application 32237/84 by Orborn employs bentonite in a porous cylinder to drive a diaphragm valve. None of these hygrostats is suitable for use in the ground because they all imbibe water like tensiometers and hold it in the highly hygroscopic materials in a manner atypical of normal soils. The selected materials have poor repeatability and the associated semipermeable membranes often become blocked by algal, fungal and bacterial growth. The pistons tend to seize either from the microorganisms or the sub-micron particles of the bentonite clay finding their way between the piston and cylinder.

U.S. Pat. No. 3,874,590 to Gibson discloses a buried hydrostat that uses a long vertical tubular hydroscopic element of nylon, cellulose acetate or vulcanised fibres encased in a perforated water-impervious tube or casing. A water-impervious actuator rod extends through the tubular element and has an enlarged head that rests on the top of the element so that the rod moves with it as it expands. The bottom of the rod slides in a cylinder to operate a pilot valve for the main irrigation system. The use of multiple concentric tubular elements is proposed as a way of magnifying the movement of the rod of a reasonable length. Though the hygroscopic materials selected are likely to be durable in soil, their repeatability—except for nylon—is dubious. Since nylon is only slightly hydroscopic, long elements (or series-connected elements) are needed. The complex arrangement of concentric tubes, rod, casing and valve is expensive to fabricate, will tend to jam because of lateral expansion and buckling and because of the intrusion of dirt into the close-fitting parts. Rapid equilibration of moisture between the element and the surrounding soil is inhibited by the multi-layered nature of the element, the use of a casing, the poorly hydroscopic nature of nylon (the preferred material), and the (intentional) pooling of water in the tubes.

While none of the above devices were said to be suited for use with pot-plants, U.S. Pat. No. 3,512,712 discloses such a device. It uses a hollow column of wood as the hydroscopic element but, being far too bulky to be buried in the soil of a flower-pot, the element is mounted beside the pot and water from the soil in the pot is wicked-up into the tube, causing the length of the tube to vary and to operate a moisture gauge and/or a valve that regulates the flow of water to the pot. Not only is such a device bulky and expensive, but its control function will be inherently poor as wood has poor repeatability as a hydroscopic material and is prone to fungal attack. The dampness of the element will be determined more by atmospheric humidity than by the moisture content of the flower-pot soil and evaporation from the element will cause the deposition of soil-salts.

OBJECTIVES OF THE INVENTION

It is the general object of this invention to provide a hygrostat, hygrostat system and method that will be free of one or more of the problems mentioned above. A more specific objective is to provide improved means suitable for use in regulating the flow of water to pot-plants. It is, however, also desirable that the hygrostats be applicable for use above ground as rain monitors as well as under the ground as soil moisture monitors for automatic irrigation systems. However, it is not essential that every embodiment of this invention meets every one of these objectives and desiderata.

SUMMARY OF THE INVENTION

From one aspect, this invention is based upon the realization that the hydroscopic element of a hydrostat suited for burial in the soil needs to be a coherent synthetic polymeric material in the form of a relatively thin solid strip or disc with its two principal sides comprising most of its surface area, and that such an element should be arranged so that both sides have direct and substantially unrestricted contact with the soil, when the hygrostat is buried. This form of element arranged in this way allows close to optimum moisture exchange between the element and the soil and the use of a synthetic polymer makes it possible to ensure repeatability and resistance to degradation (eg. by soil micro-organisms) over long periods of time.

The synthetic polymeric material can be a coherent polyamide like nylon, as is known in the art, but nylons generally are not sufficiently hygroscopic to make the simple and compact hygrostats for flower-pots. Polyamide copolymers (such as polyether block amides) are preferred as their hygroscopic properties can be precisely engineered. We found them to have good strength, resistance to soil microorganisms, and to have high repeatability as hygrostats. Polyether block amides that take up between 50% to 150% by weight of water after immersion for 24 hours at 25° C. have been found most suitable and are obtainable from major manufacturers such as Hoechst, General Electric, duPont, Elf Atochem and Sumitomo.

From another aspect, the invention may also be based upon the appreciation that there should be no lost motion at the ends of the hygroscopic element, even under the driest conditions, so that soil cannot interpose itself at either end of the element. Though a spring can be used, it adds to the buckling forces on the element and must be isolated from the soil in order to work properly. Instead, holes, hooks, notches or the like are preferably molded into the ends of the strip-form elements so that they can be attached (directly or indirectly) to a frame at one end and to a diaphragm, valve or transducer at the other. It may then be desirable to provide means to inhibit the opening or disengagement of hooks or the like formed on the element as it expands or contracts. Conveniently, the valve or transducer is housed in a chamber and isolated from the soil by the flexible diaphragm, to which one end of the element may be attached. If a spring is employed, it should be contained within the chamber or molded integrally with the diaphragm.

Where a strip-like element is employed, it is envisaged that guide means may be used to resist the tendency of the strip to buckle as it expands to operate the valve or transducer. For example, a pair of side-guide rails fixed at one end to the diaphragm by a common foot but free to slide at the other end in a frame may be used, the portion of the element remote from the diaphragm being free to slide between the guide rails as the element expands and contracts.

Undesirable buckling of the element can also be reduced or avoided by forming it as a curved ('pre-buckled') strip or disc arranged so that its ends (or its periphery) are (or is) held in a frame and so that movement of its center effects the operation of the valve or transducer as the element expands or contracts. Again, it is desirable to ensure that (i) soil is able to make direct and ready contact with both sides of the strip or disc and that (ii) there can be no lost-motion as it expands or contracts so that soil cannot intrude at the interface.

Hygrostats formed as indicated will normally be buried in soil so that their hygroscopic elements are substantially vertical and the diaphragm (where employed) is above the element in the case of a strip or to one side of the element in the case of a disc. Arranged in this way, water will not be able to pool on the element or diaphragm. But if the hygrostats are intended to be mounted above ground and are fitted with switches to inhibit sprinkler systems after rain, it will generally be desirable for the diaphragms to be arranged horizontally below the elements so that, in the case of a strip-form element, rain can pool on the diaphragm and, in the case of a dish-form element, rain can pool in the element itself. However, it may be sufficient for some open-air applications (in hot-houses, for example) for the hygroscopic element to operate a hermetically-sealed switch without the need to house the switch in a separate chamber behind a diaphragm.

From another aspect, the invention comprises a hygrostat system suitable for use with pot-plants and comprising a hygrostat having a water-flow valve operable by the expansion and contraction of a hydroscopic element, the valve being housed within a sealed chamber arranged above or at the side of the element, a water inlet and outlet being connected to the valve, and water distribution means comprising a substantially horizontal water distributor plate having an upper surface, a water outlet orifice in or on the upper surface, and comprising a substantially rigid connector linking (or adapted to link) the plate and the hygrostat such that the plate is positioned above and to one side of the hygrostat, the connection including a conduit for connecting the valve outlet to the orifice. The plate may be formed at least in part from hydrophobic porous material through which water flowing from the orifice may percolate under gravity. The portion of the connector near the plate is preferably arranged to slope downwards toward the plate so that water flowing from the plate does not tend to track along the exterior of the connector to the hygrostat.

From yet another aspect, the invention encompasses a method of regulating the supply of water to a pot plant comprising the steps of supplying water to a buried hygrostat unit and leading water flowing from that unit to the surface of the soil at a fixed distance from said unit and, optionally, releasing the water into and through a porous hydrophobic plate on the surface of the soil.

BRIEF DESCRIPTION OF THE DRAWINGS

Having broadly portrayed the nature of the present invention, five embodiments of the invention will now be described by way of illustration only. In the following description, reference will be made to the accompanying drawings in which:

FIGS. 3A and 3B respectively, front and side sectional elevations of the unit of FIG. 1, the section of FIG. 3B being a view taken along section line 3B—3B of FIG. 3A.

FIG. 6 is a sectional front elevation of a hygrostat unit comprising the third embodiment of this invention.

FIG. 7 is a sectional elevation of a hygrostat unit comprising the fourth embodiment of this invention.

DETAILED DESCRIPTION OF THE PREFERRED EMBODIMENTS

Figure 1:
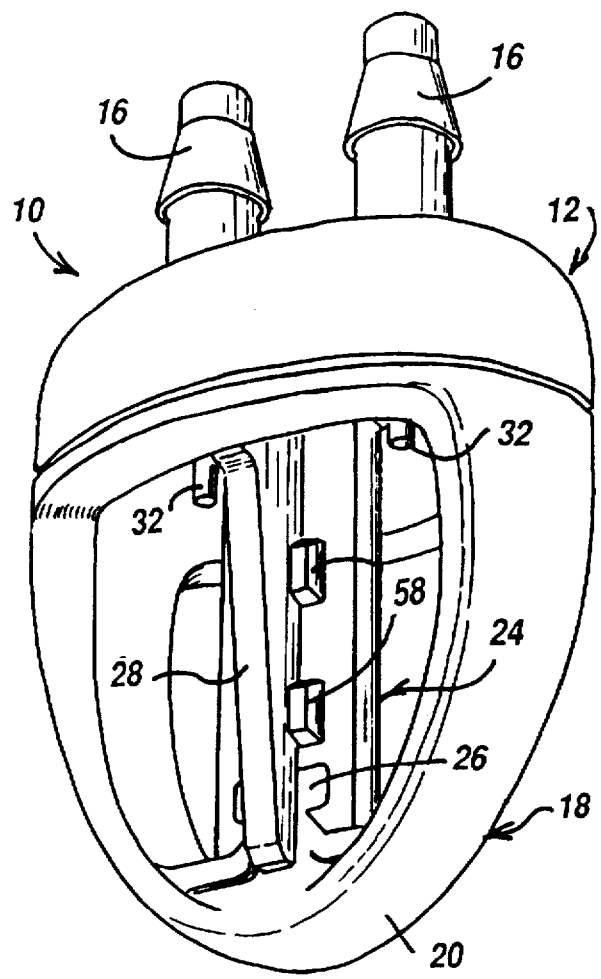
FIG. 1 is a perspective view from below and the front of a hygrostat comprising the first embodiment of this invention.
Figure 2:
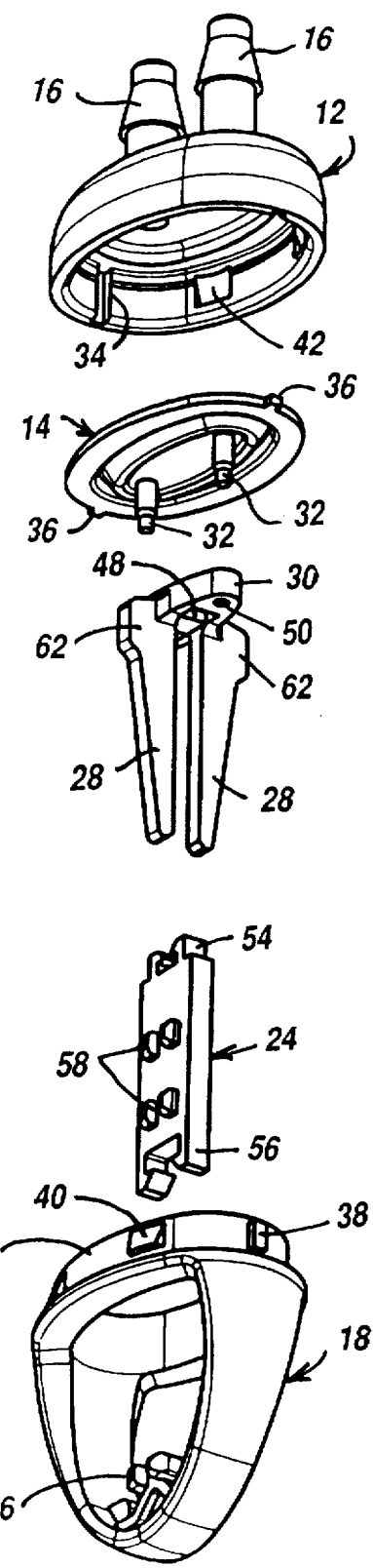
FIG. 2 is an exploded perspective of the hygrostat of the first embodiment.

Referring to FIGS. 1–3, the hygrostat unit 10 of the first embodiment basically comprises: an upper chamber 12 shaped like an inverted cup which is closed by a diaphragm, having water inlet/outlet spigots 16 extending from its top; a lower frame 18 that is shaped like an inverted stirrup having a lower arch 20 and an integrally-molded upper snap-ring 22 that fits inside the rim of chamber 14; a strip-form polymeric hydroscopic element 24 clipped at its lower end to a key-stone protrusion 26 at the bottom of frame 18; and, a pair of guide rails 28 on each side of element 24 serving to stiffen the element against buckling, the upper ends of rails 28 being joined together by a foot 30 to which the upper end of element 24 is clipped and attached to diaphragm 14 by 'pull-through' studs 32, the lower ends of rails 18 being free to slide over keystone 26 while being laterally located thereby.

With particular reference to FIGS. 2, 3A and 3B, it will be seen that chamber 12, diaphragm 14 and snap-ring 22 are of an elliptical shape and that keyways 34 are formed on the inside walls of the ends of chamber 12 to take corresponding locating keys 36 on diaphragm 14 and keys 38 on snap-ring 22. Wedge-like catches 40 are molded into the external periphery of snap-ring 22 to engage corresponding indents 42 on the interior surface of the wall of chamber 12. When snap-ring 22 is pushed home into chamber 12, the periphery of diaphragm 14 is clamped between the edge of ring 22 and the chamber to form a fluid-tight seal (see FIGS. 3A and 3B).

Molded integrally with diaphragm 14 on its inner (upper) face are a pair of cone valve-stems 44, which are aligned with the bores of spigots 16 when the diaphragm is in-place within chamber 12. The studs 32 are molded in-line with cones 44 on the outside (lower) face of diaphragm 14 and are pulled through holes 48 (FIG. 2) in foot 30 to secure diaphragm 14 to the foot, eliminating lost-motion therebetween. A central recess 50 is formed in foot 30 to accommodate the upper end of the hydroscopic element 24, a bar 52 being formed across recess 50 so that hooks 54 molded on the upper end of element 24 may be clipped over the bar to secure element 24 to the bar (and thus the diaphragm) without lost motion. A further pair of hooks 56 are molded on the lower end of element 24 to engage key-stone 26 of frame 18 in a similar manner. In this way, lost motion between element 24 and frame 18, as well as between the element and the diaphragm 14, is eliminated so that soil cannot intrude as the element contracts.

In this example, the strip-form element 24 is injection-molded from a commercially available hydroscopic polyether block amide copolymer capable of absorbing about 80–100% of its weight in water at 25° C. over a 24 hour period. A strip of this material will increase in length by between 15% and 25%. It will retain much of its strength even when fully saturated. For the hygrostat of this example, which is intended to be buried in the soil of a pot-plant, the element may conveniently be between about 20 mm long, 8 mm wide and 2 mm thick so that the surface area of the large side faces accounts for nearly 75% of the total surface area of the element. The element will normally operate between about 20% and 75% saturation and vary in length sufficiently to raise cones 44 about 1.5 to 2 mm from their ports at less than 20% saturation and push them firmly into the ports at more than about 70% saturation. With a regulated low-pressure water supply and the valves open, a suitable water flow-rate for most pot-plants would be about 500 ml per hour, a cycle time of some hours being desirable.

As already noted, guide rails 28 serve to stiffen element 24 against buckling when it is wet and cones 44 are pressed into the bores of spigots 16. Other measures to reduce buckling are also taken: first, rows of stops 58 are molded on each side face of element 24 to better locate it with respect to rails 28 (FIGS. 1 & 2); second, guide slots 60 (not shown in FIG. 1 for clarity, see FIG. 4) are formed on the sides of key-stone 26 to better locate the rails with respect to frame 18; third, the upper ends of rails 28 are enlarged outward to form wings 62 that are guided by the inside walls of snap-ring 22 (see FIG. 3B); and, fourth, the diameter of the bores in spigots 16 is preferably less than 2 mm and a pressure reducer is included in the inlet line so as to reduce the hydrostatic force on element 24 (as well as restrict the maximum rate of water flow to the soil). While means for preventing hooks 54 and 56 from opening when element 24 is under tension will be described in the third embodiment, it can be noted that shoulders 64 (FIGS. 3A and 4) near keystone 26 can serve this function for lower hooks 56.

To assemble the hygrostat unit 10, element 24 is slipped between guide-rails 28 from their open ends, hooks 54 on the upper end of element 24 are clipped over bar 52 in recess 50 of foot 30, studs 32 on the external face of diaphragm 14 are pulled through holes 48 in foot 30 to secure the diaphragm to the foot and to the upper end of element 24. This sub-assembly is then located within chamber 12 so that cones 44 are located in the bores of spigots 16, snap-ring 22 of frame 18 is entered into chamber 12 while rails 28 are guided into slots 60 and hooks 56 on the lower end of element 24 are manipulated around keystone 26, and finally, snap-ring 22 is pressed home into chamber 12 to form the seal between the periphery of diaphragm 14 and the chamber 12.

It will be noted that the two side faces of the strip-form element which account for most of its surface area, are arranged opposite much larger openings in the sides of the frame so that direct contact between the soil and the element is facilitated. As the element is thin, its surface area is significantly greater than its volume so that the moisture content to that of the surrounding soil rapidly reaches equilibrium, whether it is taking-in or releasing water.

Figure 4:
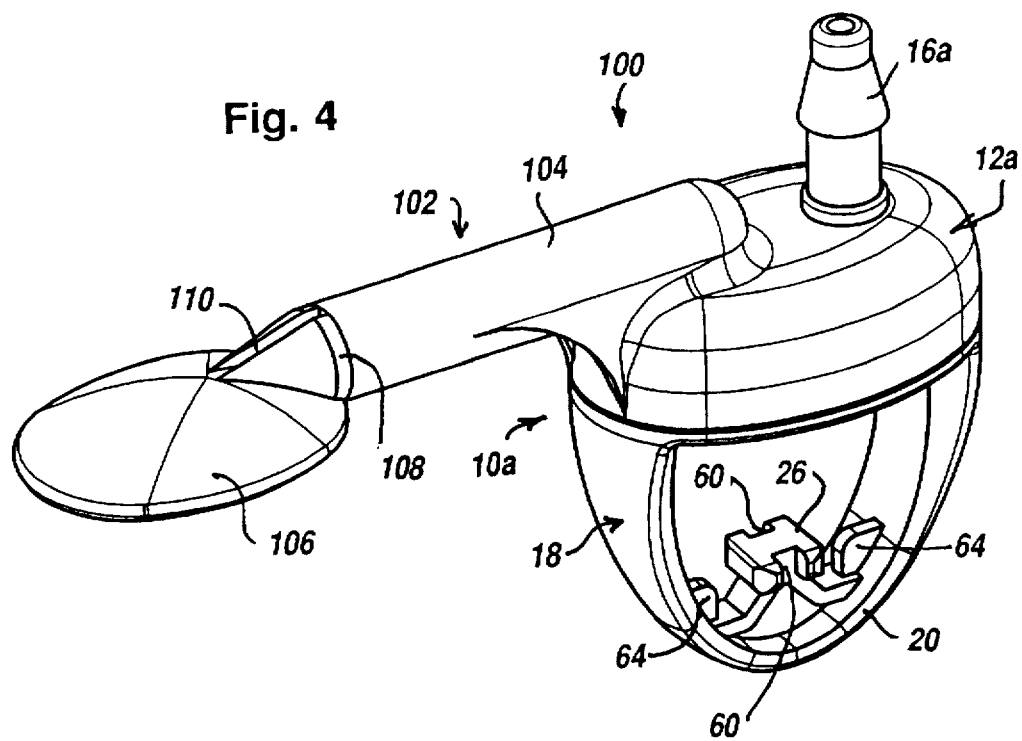
FIG. 4 is a perspective view from above of a hygrostat system of the second embodiment (with the sensing element removed).
Figure 5:
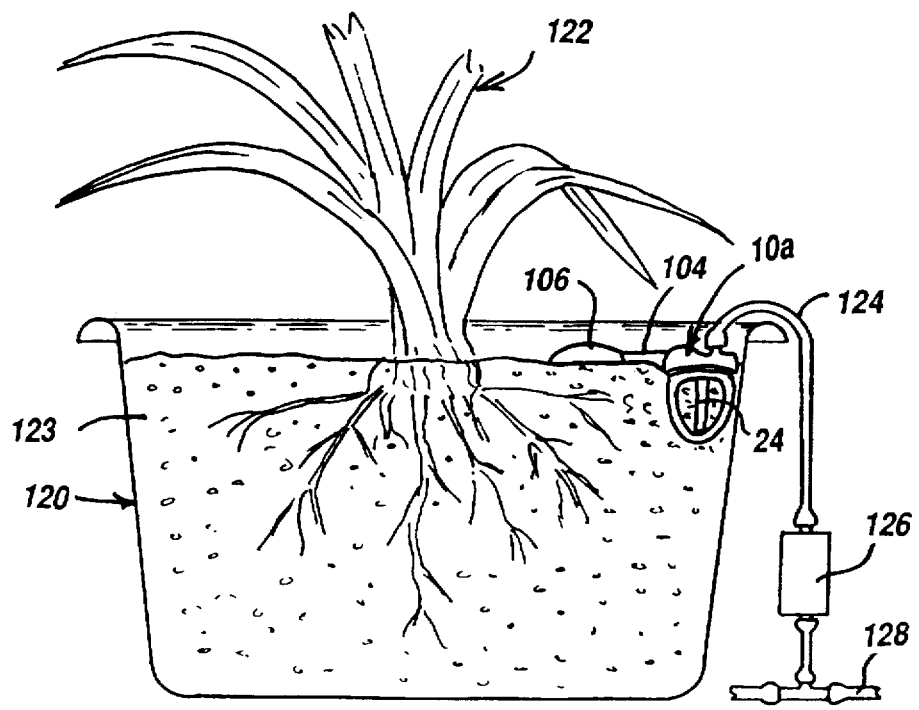
FIG. 5 is a diagrammatic sectional side elevation of a potted-plant with the hygrostat system of FIG. 4 installed.

The second example of the invention, illustrated in FIGS. 4 and 5, is a hygrostat system 100 embodying (i) a hygrostat unit 10a of the first embodiment and (ii) a water distribution means 102. FIG. 4, however, is illustrated with the hydroscopic element (24) and the rails (28) omitted to better illustrate the configuration of the key-stone 26, groove 60 and shoulders 64. The chamber 12a is, however, molded somewhat differently from that of the first embodiment: only one spigot 16a extends upwardly from the chamber top and that serves as the inlet; the outlet is formed by a horizontal tube 104 molded integrally with the chamber so as to extend sideways therefrom (i.e., substantially coplanar with the arch 20 of frame 18). A substantially horizontal water-spreader or distributor plate 106 has a stub 108 that is pressed into the end of tube 104 and, in this example, has a slot-like outlet orifice 110 formed at the junction of stud 108 and plate 106 through which water from hygrostat 10a is discharged. Thus, tube 104, plate 106 (and its stub 108 and orifice 110) together make up the water distribution means 102.

FIG. 5 indicates the manner in which the hygrostat system of the second example may be used to regulate the supply of water to a pot-plant. Pot 120 contains a plant 122 in soil 123. The system 100 is arranged so that hygrostat 10a is buried in the soil near the side of pot 120 and distributor plate 106 is located on the surface of the soil between the plant 122 and the hygrostat. Inlet spigot 16a is connected via tube 124 and pressure reducer 126 to a water supply line 128, the pressure to the hygrostat being limited, for example, to about 200 kN/m² (about 30 psi). When burying the hygrostat unit, care should taken to ensure that the soil is in intimate contact with both sides of the hydroscopic element 24. If the soil is rich and loamy (as in a potting mix) some of it may be pressed into the sides of the hygrostat frame before it is buried to ensure that it contacts the element. If the soil has a high clay content or otherwise tends to cake when dry, it is desirable to surround the hygrostat with potting mix or fine sand so that the earth does not cake onto the element when dry. By arranging for the outlet water to flow onto the surface of the soil at a fixed distance from the buried hygrostat, the correct operation of the hygrostat can be better assured, and, visual confirmation of watering is provided to the householder so that there will be less temptation to dig up the hygrostat to check that it is working (given that the rates of water-flow are very low even when the valve is open).

There can be a danger with the hygrostat of the first embodiment for hooks 54 and 56 to pull off bar 52 and key-stone 26 (respectively) when element 24 dries-out. The third embodiment, shown in FIG. 6, illustrates one way in which this danger can be addressed in a hygrostat of the same basic design. In this case, the hygrostat 210 has chamber 212, diaphragm 214, a central inlet spigot 216 and an offset outlet spigot 217, a stirrup-like frame 218, guide-rails 228 (see FIG. 8) joined by foot 230 and a strip-form hygroscopic element 224. A T-slot 270 is formed in the bottom of frame 18 instead of key-stone 26 of the first embodiment, the lower end of element 224 having the shape of a corresponding T-shape lug, which is engaged with slot 270 by sliding the lower end of the element transversely. Hooks 254 are formed on the upper end of element 224 facing outward rather than inward (as in the first embodiment). They enter the central hole of foot 230 and grip ledges on the outsides of the hole (rather than the central bar 52). Hooks 254 are deflected towards one another (rather than apart) to allow them to enter the foot. To ensure that hooks 254 cannot be forced toward one another (releasing foot 230) when element 224 is under tension, a protrusion 274 is formed on the bottom face of diaphragm 214 opposite the single central cone-valve 244. It might be noted that the same principle could be used with the inwardly-facing hooks (54) of the first embodiment, if a pair of downward protrusions are formed on the diaphragm (14) to fit at the back of the hooks. As already noted, the opening of lower hooks 56 of the first embodiment can be prevented by bringing shoulders 64 closer to the keystone 26 and entering the lower hooks (56) laterally into the resultant slot.

The fourth embodiment of the application of the principles of the invention is the hygrostat unit 300 shown in FIG. 7, which incorporates a hydroscopic element in the form of a thin circular dished-disc (or dish) 302, the peripheral edge 304 of which is held by six posts 306 that rise from a common base-ring 308 (the posts and base-ring forming the open-frame of this example). Ring 308 functions as the snap-ring (22) of the first example, clipping to the rim of a flat circular chamber 310 to seal the periphery of a diaphragm 312. An inlet pipe 314 is integrally molded with the back of chamber 310 and leads to a central port 316, which may be closed by a cone protruding from the inner face of diaphragm 312. Similarly, an outlet pipe 320 is molded on the back of chamber 310 and communicates with an outlet port 322. The front face of diaphragm 312 also carries a central cone-like protrusion 324 that extends through a hole in the center of dish 302 and is turned over (by the use of a hot object, for example) to firmly attach the diaphragm 312 to the hygroscopic element 302 (so there can be no lost motion there-between).

Lost motion between posts 306 and periphery 304 of element 302 can be prevented in various ways. That illustrated uses compression spring 326 to keep periphery 304 pressed into the slots in posts 306, and spring 326 also assists in centering cone 318. However, periphery 304 may be positively secured to the posts by pins fitted into holes formed in the ends of the posts and driven through periphery 304. Alternatively, the slots in posts 306, which engage the periphery may be of key-stone shape and periphery 304 may be molded with a corresponding section. Cut-outs may then be formed in the periphery so that it can be engaged with the post slots and then rotated with respect to the posts into position.

When hygrostat unit 300 is buried in the soil to function like that of the first example, it will be preferable for disc/dish element 302 to be mounted substantially vertically and, once again, for care to be taken to ensure the surrounding soil contacts both the concave and the convex sides of hygroscopic element 302. Obviously, the geometry of the element ensures that (i) its surface area to volume ratio is high and (ii) the soil can contact practically all of its surface so, again, rapidly reaching equilibrium with soil moisture.

Figure 8:
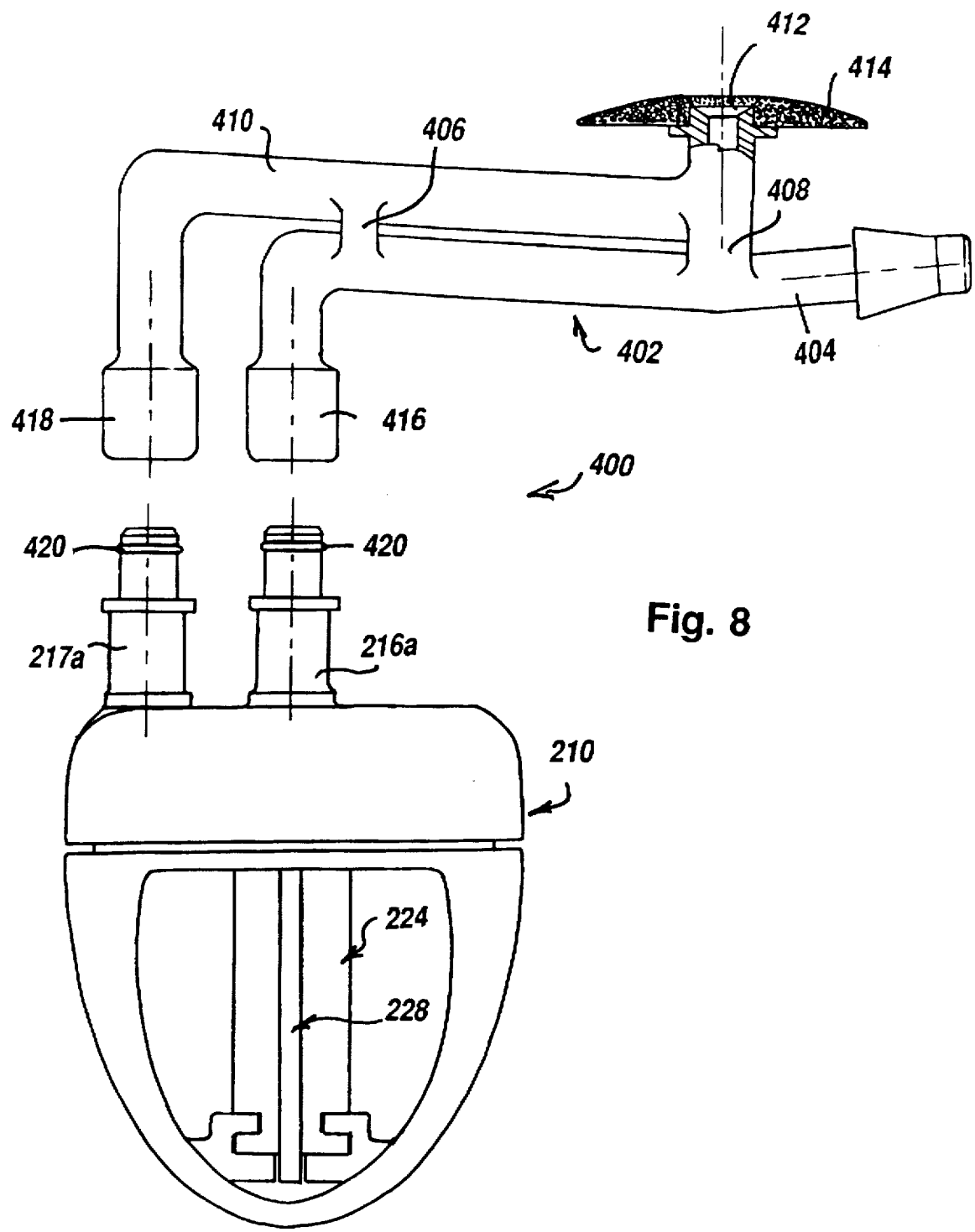
FIG. 8 is an elevation of a hygrostat system which forms the fifth embodiment of the application of this invention.

The fifth and final embodiment, shown in FIG. 8, is the hygrostat unit 210 of the third embodiment as part of a hygrostat system 400 using a different type of water distributor 402, which consists of a generally horizontal inlet pipe 404 attached by ties 406 and 408 to an outlet pipe 410 that terminates, at its output end in an upwardly-facing orifice 412. A porous distributor plate 414 of hydrophobic material (e.g., sintered teflon or a ceramic) surrounds orifice 412. A downwardly-turned socket 416 is formed on the outlet end of inlet-pipe 404 and a similar socket 418 is formed on the inlet-end of outlet-pipe 410, the sockets being arranged to mate with spigots 216a and 217a of hygrostat 210. In this example, however, the spigots are modified to take O-rings 420 for a water-tight push-fit into sockets 416 and 418 in the manner well known in the art.

In operation, the system of FIG. 8 works essentially like that of FIGS. 4 and 5, except that pipes 404 and 410 are buried and angled downward so that water from orifice 412 and plate 414 will not tend to track back along the pipes to hygrostat 210. Also, by employing a hydrophobic and porous distributor plate, water from the orifice is delivered to the soil over a wide area without the water wicking upward and evaporating. The length and configuration of the distributor means 402 can be varied to suit that of the pot-plant though, if a large pot is to be watered, it will be generally preferable to employ more than one hygrostat system.

It will be appreciated that hygrostat units and systems described as examples can be readily made small and cheap so that one or more can be used for each pot to be watered. They are inherently reliable since the synthetic polymeric hygroscopic elements will not degrade in the soil, like natural materials, and having no lost-motion associated with the expansion and contraction of the elements, their operation is not likely to be affected by the ingress of soil into the 'mechanism'. Importantly, however, by employing a thin strip-like or disc-like hygroscopic element so that a large proportion of its surface area is in direct and unobstructed contact with the soil, rapid equilibrium of soil and element moisture is ensured and appropriate cycling of water flow to the soil and the plant(s) is effected.

However, many modifications and variations to the examples can be made without departing from the scope of the invention as defined by the following claims. For example, it is envisaged that a dished strip element could be used in the unit of the fourth embodiment instead of a disc, provided the frame was appropriately modified. Also, and as already indicated, the position transducer can simply be an electrical switch arranged in the chambers of the hygrostat unit so as to be operated by the movement of the hygroscopic element. In this form, the units can be mounted above ground and used to inhibit sprinkler systems during rainy periods. Thus, the hydrostat unit of the first embodiment could be mounted with its frame uppermost so that rain will collect in the chamber above the diaphragm and keep the hygroscopic element extended until it evaporates. Similarly the unit of the third embodiment could be mounted with its concave side uppermost to collect rainwater and inhibit a sprinkler until it evaporates and the disc dries out. Where a moisture level indicator is required instead of a switch, it will be appreciated that a linear transducer, pressure sensor or equivalent device can be housed in the hygrostat chamber instead of the switch or valve.

We claim:

1. A hygrostat adapted for burial in soil, comprising:
   a frame having a first end portion and a second end portion, and defining substantially unobstructed openings extending between the first and second end portions;
   a water flow-control valve, supported by the second end portion of the frame; and
   a hygroscopic element formed from a coherent synthetic polymer and arranged between the first end portion of the frame and the water flow-control valve, wherein the hygroscopic element expands and contracts upon uptake and release of water, expansion and contraction thereof controlling operation of the device water flow-control valve; and
   wherein the hygroscopic element has two principal opposing surfaces that comprise a majority of the surface area thereof, the principal surfaces being exposed through the frame openings so that both principal surfaces are adapted to directly contact the soil through the frame openings upon the hygrostat being buried in soil.

2. A hygrostat according to claim 1, wherein the hygroscopic element is formed from a polyether block amide copolymer having a water absorption of between 50% and 150% by weight of water after immersion in water for a period of 24 hours at 25° C.

3. A hygrostat according to claim 2, wherein:
   the second end portion of the frame defines a chamber within which the device water flow-control valve is located, the chamber having an opening facing the first end portion of the frame, and further comprising:
   a flexible, water-impermeable diaphragm covering the chamber opening,
   wherein the hygroscopic element has a distal end attached to the first end portion of the frame with no lost-motion therebetween upon contraction of the hygroscopic element, and has a proximal end attached to the diaphragm with no lost motion therebetween upon contraction of the element, and
   wherein movement of the diaphragm caused by expansion and contraction of the hygroscopic element actuates the device water flow-control valve.

4. A hygrostat according to claim 3, further comprising a pair of elongate guide rails each having a proximal end located near the diaphragm and a distal end opposite the proximal end, and a foot member joining the proximal ends of the guide rails,
   wherein the hygroscopic element is of strip form and is located between the guide rails,
   wherein each guide-rail is arranged to slidingly engage a respective one of the principal surfaces of the hygroscopic element,
   wherein the foot member is attached to the diaphragm so as to move therewith, and
   wherein the distal ends of the guiderails are located at the first end portion of the frame and are restrained from laterally moving away from each other.

5. A hygrostat according to claim 4, wherein the distal end of the hygroscopic element is mechanically interlocked with the first end portion of the frame and the proximal end thereof is mechanically interlocked with the foot member.

6. A hygrostat according to claim 2, wherein the second end portion of the frame defines a chamber within which the device water flow-control valve is located, the chamber having an opening facing the first end portion of the frame, and further comprising:
   a flexible, water-impermeable diaphragm covering the chamber opening,
   wherein the hygroscopic element is disc shaped and arranged generally parallel to the diaphragm, with a center portion of the disc adjacent to the diaphragm, and is adapted to deflect the diaphragm into the chamber and to actuate the device water flow-control valve upon expansion of the disc,
   wherein the periphery of the disc is located at the first end portion of the frame, and wherein the first end portion of the frame comprises a plurality of posts arranged in spaced relation around the periphery of the chamber.

7. A hygrostat according to claim 6, wherein the center portion of the disc is attached to the diaphragm to prevent lost motion therebetween, and the periphery of the disc is engaged with the posts to prevent lost motion between the frame and the disc.

8. A hygrostat according to claim 6, further comprising a spring positioned within the chamber, biasing the diaphragm toward the disc, thus biasing the disc against the posts, to prevent lost motion between the disc and the diaphragm.

9. A hygrostat according to claim 3, wherein:

the diaphragm has a peripheral portion abutting a peripheral ledge formed around the opening of the chamber, the second end portion of the frame is divided into two parts, one part thereof forming the chamber with an opening and the other part thereof forming a pressure ring adapted to bear against the peripheral portion of the diaphragm and to hold it against the ledge in a water-tight manner, and the one part of the second end portion of the frame is adapted to be engaged with the other part in snap-fit engagement to forcibly hold the pressure ring against the peripheral portion of the diaphragm.

10. A hygrostat adapted for burial in soil, comprising:

a hygroscopic element formed from a coherent polyether block amide copolymer capable of absorbing between 50% and 150% of its own weight in water during immersion in water over a period of 24 hours at 25° C.; and a water flow-control valve operably connected to the hygroscopic element and operable by the expansion and contraction of the hygroscopic element, wherein the majority of the hygroscopic element surface is exposed to directly contact the soil upon the hygrostat being buried.

* * * * *